United States Patent
Getty et al.

(10) Patent No.: US 9,624,147 B2
(45) Date of Patent: Apr. 18, 2017

(54) PRODUCTION OF SHORT CHAIN PERFLUOROALKYL IODIDES FROM HIGHER ORDER TELOMERS

(71) Applicant: THE CHEMOURS COMPANY FC LLC, Wilmington, DE (US)

(72) Inventors: Stephen James Getty, Wilmington, DE (US); George Murray Volker, Lumberton, TX (US); Pelin Hacarlioglu, Philadelphia, PA (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 14/922,237

(22) Filed: Oct. 26, 2015

(65) Prior Publication Data

US 2016/0122266 A1    May 5, 2016

Related U.S. Application Data

(60) Provisional application No. 62/072,688, filed on Oct. 30, 2014.

(51) Int. Cl.
*C07C 17/361* (2006.01)
*C07C 19/16* (2006.01)

(52) U.S. Cl.
CPC ............ *C07C 17/361* (2013.01); *C07C 19/16* (2013.01)

(58) Field of Classification Search
CPC .................................................. C07C 17/361
See application file for complete search history.

(56) References Cited

U.S. PATENT DOCUMENTS

| | | |
|---|---|---|
| 3,132,185 A | 5/1964 | Parsons |
| 3,234,294 A | 2/1966 | Parsons |
| 5,268,516 A | 12/1993 | Bertocchio et al. |
| 8,258,354 B2 | 9/2012 | Jacobson et al. |

FOREIGN PATENT DOCUMENTS

DE    4410551 A1    9/1995

OTHER PUBLICATIONS

Probst et al., Journal of Fluorine Chemistry, 47, (1990), 163-173.

*Primary Examiner* — Jafar Parsa
*Assistant Examiner* — Medhanit Bahta

(57) ABSTRACT

An improved process for producing perfluoroalkyl iodides of formula (I)

$$F(CF_2CF_2)_n\text{—I} \qquad (I)$$

wherein n is an integer from 2 to 3, wherein the improvement comprises thermolyzing at least one perfluoroalkyl iodide of formula (II), optionally in the presence of perfluoroethyl iodide, formula (III)

$$F(CF_2CF_2)_m\text{—I} \qquad (II)$$

$$F(CF_2CF_2)_p\text{—I} \qquad (III)$$

wherein m is an integer greater than or equal to 4, and p is 1, wherein a) the molar ratio of formula (III) to formula (II) is less than 1.0, b) the residence time is from about 0.1 to about 10 seconds, and c) the temperature is from about 450° C. to about 500° C.

12 Claims, 3 Drawing Sheets

PRODUCTION OF SHORT CHAIN PERFLUOROALKYL IODIDES FROM HIGHER ORDER TELOMERS

BACKGROUND OF THE INVENTION

Long chain perfluoroalkyl iodides are prepared by the conventional telomerization of tetrafluoroethylene (TFE) with pentafluoroethyl iodide, which can be thought of, formally, as the insertion of TFE into the C—I bond. This telomerization yields perfluoroalkyl iodides with a chain length distribution of varying TFE insertions. Most current processes produce chain lengths from 8 carbons to 20 carbons in length. Perfluoroalkyl iodides have many uses as a key starting material in the preparation of surface modifying products, such as repellants, stain and soil resist agents, as well as surfactants. The current trend in these end use markets is to exclude the 8-carbon and longer chain lengths, and focus on shorter chain perfluoroalkyl iodides as starting materials. This work specifically targets the production of straight chain perfluorobutyl iodide and perfluorohexyl iodide (C4-I and C6-I perfluoroalkyl iodides, respectively) from higher order (longer chain) perfluoroalkyl iodides, such as perfluoro-octyl iodide (C8-I) or mixtures of C8-I and higher homologue perfluoroalkyl iodides.

Bertocchio et al., in U.S. Pat. No. 5,268,516, disclose a process for preparation of shorter chain perfluoroalkyl iodides in a thermal telomerization of TFE with pentafluoroethyl iodide or heptafluoroisopropyl iodide by adjusting feed concentration and location of the TFE feed. This process is distinct from that reported herein in that it is a telomerization of TFE.

Becker et al., in German Patent Application DE 4,410,551A1, disclose a process for preparing short chain perfluoroalkyl iodides by reaction of longer chain perfluoroalkyl iodides (greater than 8 carbons in the perfluoroalkyl) with shorter chain perfluoroalkyl iodides (6 carbons or less in the perfluoroalkyl) to produce the desired short chain perfluoroalkyl iodides as well as inert perfluoroalkanes as a by-product. Becker et al., added iodine in the process to increase selectivity of the perfluoroalkyl iodide over the perfluoroalkanes, although this also decreased the overall conversion of reactants to the desired products. The addition of iodine ($I_2$) increases the presence of water into the system, potentially producing a second inert byproduct, 1-hydroperfluoroalkanes.

The use of iodine causes several issues in processes. Iodine introduces opportunities for line plugs, a need for iodine recycling and neutralization, and the potential hydrogen iodide formation. As observed by Becker, iodine may also lead to production of unwanted inert by-products, such as 1-hydroperfluoroalkanes.

U.S. Pat. No. 8,258,354 B2 (to Jacobson et al.) discloses a process to produce $F(CF_2CF_2)_2$—I and $F(CF_2CF_2)_3$—I from $F(CF_2CF_2)_m$—I and $F(CF_2CF_2)_p$—I, where m is an integer greater than or equal to 3, and p is an integer equal to or lower than 2, and which process is operative without the use of added iodine.

Despite these disclosures, the yields of $F(CF_2CF_2)_2$—I and $F(CF_2CF_2)_3$—I are borderline in terms of being high enough to enable a commercially viable process. There is a need for a process for the production of shorter chain perfluoroalkyl iodides, having high selectivity for $F(CF_2CF_2)_2$—I and $F(CF_2CF_2)_3$—I (for example, a combined selectivity for $F(CF_2CF_2)_2$—I and $F(CF_2CF_2)_3$—I greater than 45% in the absence of iodine), lower selectivity for inert perfluoroalkanes and operable either in the presence or absence of iodine as a reactant. The present invention meets these needs.

SUMMARY OF THE INVENTION

The present invention provides an improved process for producing perfluoroalkyl iodides of formula (I)

$$F(CF_2CF_2)_n\text{—I} \qquad (I)$$

wherein n is an integer from 2 to 3, wherein the improvement comprises thermolyzing at least one perfluoroalkyl iodide of formula (II) optionally in the presence of perfluoroethyl iodide, formula (III), where p=1

$$F(CF_2CF_2)_m\text{—I} \qquad (II)$$

$$F(CF_2CF_2)_p\text{—I} \qquad (III)$$

wherein m is an integer greater than or equal to 4, and p is 1, wherein a) the molar ratio of formula (III) to formula (II) is less than 1, b) the residence time is from about 0.1 to about 10 seconds, and c) the temperature is from about 450° C. to about 500° C.

In an embodiment of the invention the selectivity for species (I) is greater than 45 mol %.

In an embodiment of the invention, the molar ratio of formula (III) to formula (II) is less than 0.7.

In an embodiment of the invention, the molar ratio of formula (III) to formula (II) is less than 0.5.

In an embodiment of the invention, the process is performed in the absence of a TFE trap species and the molar ratio of formula (III) to formula (II) is essentially zero. The absence of a TFE trap species means that there is no initial addition of the formula (III) species, i.e., no initial addition of perfluoroethyl iodide, perfluorobutyl iodide or perfluorohexyl iodide (C2-I, C4-I and C6-I perfluoroalkyl iodides, respectively) which may act to trap TFE liberated in the thermolysis of the formula (II) species.

In an embodiment of the invention, the temperature is from about 470° C. to about 495° C.

In an embodiment of the invention, the residence time is held at from about 0.4 to about 9 seconds.

In an embodiment of the invention, the selectivity for species (I) is greater than 45 mol % without use of iodine as a reactant.

In an embodiment of the invention, the selectivity for perfluoroalkanes is less than 20 mol %.

For each embodiment described herein, there is an embodiment for which the process is run in the absence of added iodine, and a corresponding embodiment exists for which the process is run in the presence of added iodine.

Embodiments of the present invention as described in the Summary of the Invention, and any other embodiments described herein, can be combined in any manner. Accordingly, the invention also includes embodiments which result from combinations of the elements described in each of the above embodiments.

DETAILED DESCRIPTION

Figure 1:
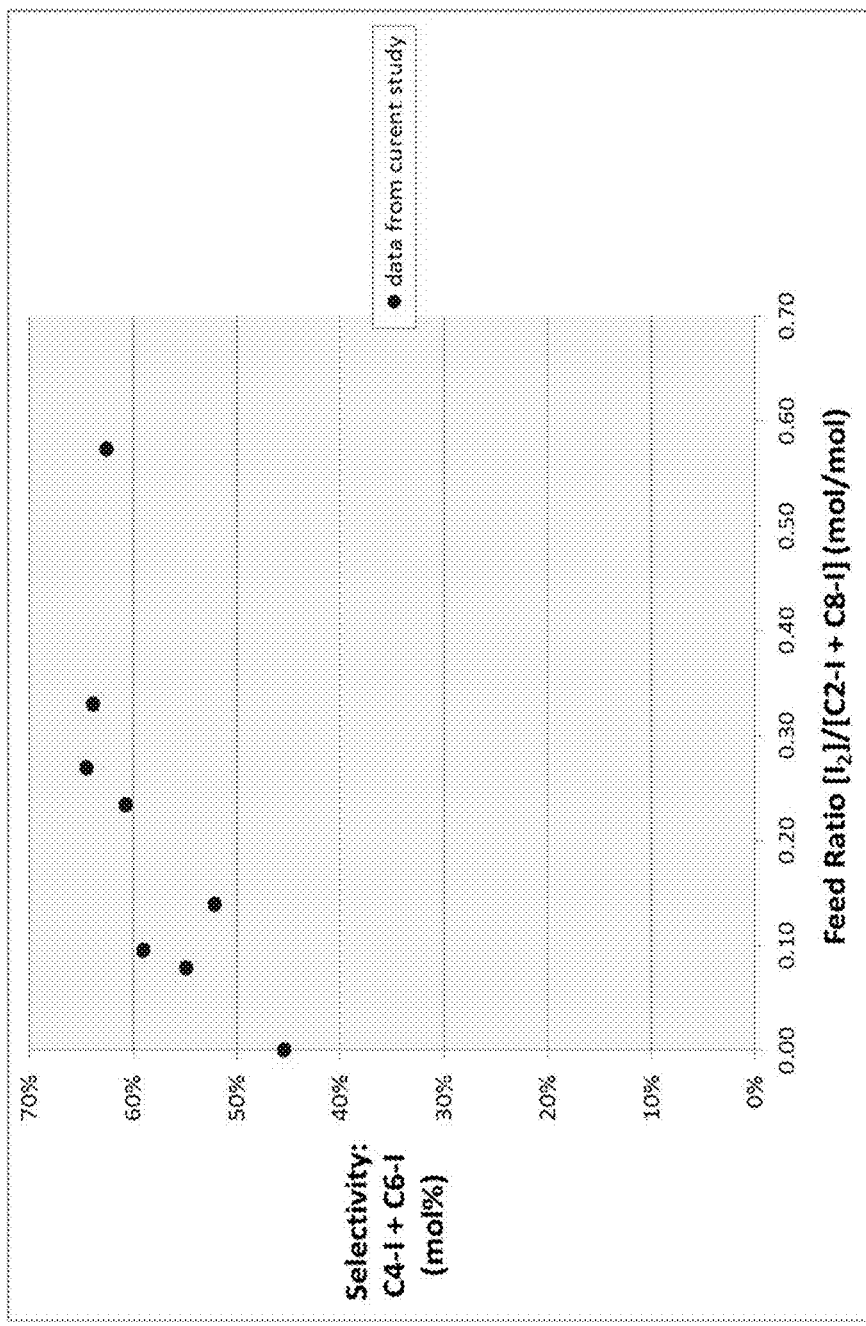
FIG. 1 shows a plot of selectivity for $F(CF_2CF_2)_2$—I (C4-I) and $F(CF_2CF_2)_3$—I (C6-I) produced in the process (y axis, in mol %) as a function of iodine addition (x axis, ratio of reactant moles of iodine to total reactant moles of $F\text{-}CF_2CF_2$—I (C2-I, formula (III), p=1) plus $F(CF_2CF_2)_4$—I (C8-I, formula (II), m=4)).

Herein trademarks are shown in upper case.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The term "perfluoroalkyl iodides" refers to fully fluorinated alkyl chains with an iodine on the terminal carbon represented by the generic formula $F(CF_2CF_2)_d$—I wherein d is equal to or greater than 1. The term "perfluoroalkanes" refers to fully fluorinated alkyl chains represented by the generic formula $F(CF_2CF_2)_d$—F wherein d is 2 to about 10. The term "1-hydroperfluoroalkanes" refers to fluorinated alkyl chains represented by the generic formula $F(CF_2CF_2)_d$—H wherein d is 1 to about 10.

Herein, the terms C4-I and C6-I are abbreviations for the straight chain perfluoroalkyl iodides: perfluorobutyl iodide, $F(CF_2CF_2)_2$—I, and perfluorohexyl iodide, $F(CF_2CF_2)_3$—I, respectively. Similarly, C2-I refers to perfluoroethyl iodide, $F(CF_2CF_2)$—I. Similarly, C8-I and C10-I refer to perfluorooctyl iodide, $F(CF_2CF_2)_4$—I and perfluorodecyl iodide, $F(CF_2CF_2)_5$—I, respectively. C8-I$_{\&+}$ refers to perfluoroalkyl iodides having C8 and longer alkyl chains (formula (II), m≥4).

Herein, "selectivity" for a product A is based on total moles of product A produced as a percentage of the total moles of all converted perfluoroalkyl iodide reactants, and is expressed as a percentage. Accordingly, the "selectivity" for species (I) is the combined mol % yield of $F(CF_2CF_2)_2$—I and $F(CF_2CF_2)_3$—I produced in the process as a percentage of the total moles of all converted perfluoroalkyl iodide reactants, expressed as a percentage.

Herein, a "TFE trap species" (or simply "TFE trap") refers to a chemical species of formula (III), capable of capturing a fragment (most commonly tetrafluoroethylene, $CF_2$=$CF_2$, TFE) cleaved from a perfluoroalkyl iodide during the reaction process. Herein, the C2-I of formula (III) functions as a TFE trap species, although C4-I and even C6-I have been used as TFE trap species in some reported works.

Herein, "mol %" means mole percentage, as commonly used in the art.

The present invention comprises an improved process for producing perfluoroalkyl iodides of formula (I)

$F(CF_2CF_2)_n$—I     (I)

wherein n is an integer from 2 to 3, wherein the improvement comprises thermolyzing at least one perfluoroalkyl iodide of formula (II) optionally in the presence of perfluoroethyl iodide of formula (III)

$F(CF_2CF_2)_m$—I     (II)

$F(CF_2CF_2)_p$—I     (III)

wherein m is an integer greater than or equal to 4, and p is 1, wherein a) the molar ratio of formula (III) to formula (II) is less than 1, b) the residence time is from about 0.1 to about 10 seconds, and c) the temperature is from about 450° C. to about 500° C.

The present invention provides for converting the undesirable longer chain perfluoroalkyl iodides of formula (II) by thermolyzing, optionally in the presence of perfluoroethyl iodide, $F(CF_2CF_2)$—I, at reaction conditions as defined above, to produce the desired perfluoroalkyl iodides of formula (I), $F(CF_2CF_2)_2$—I and $F(CF_2CF_2)_3$—I.

The present invention also selectively limits the formation of perfluoroalkanes and higher homologue perfluoroalkyl iodides where the perfluoroalkyl group in the perfluoroalkyl iodides has 10 carbons or more.

Perfluoroalkanes are produced when two perfluoroalkyl iodides react with each other, as shown in reaction scheme 1.

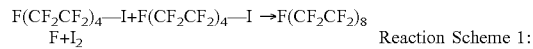

$F(CF_2CF_2)_4$—I+$F(CF_2CF_2)_4$—I →$F(CF_2CF_2)_8$
F+I$_2$     Reaction Scheme 1:

It is understood that this reaction to form a perfluoroalkane is not limited to compounds of formula (II) and can occur with any perfluoroalkyl iodides present in the process as a reactant or intermediate product. Desirably, the process of the present invention produces less than 20% perfluoroalkanes. Preferably, it produces less than 15% perfluoroalkanes, and even more preferably it produces less than 10% perfluoroalkanes.

Higher and lower homologues of perfluoroalkyl iodides can also be produced by the reaction of perfluoroalkyl iodides reactants of formula (II) as shown in reaction scheme 2.

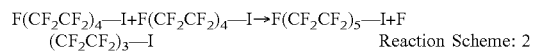

$F(CF_2CF_2)_4$—I+$F(CF_2CF_2)_4$—I→$F(CF_2CF_2)_5$—I+F
$(CF_2CF_2)_3$—I     Reaction Scheme: 2

It is understood that this reaction to form higher and lower homologue perfluoroalkyl iodides is not limited to use of compounds of formula (II) as the reactant. The reaction to form products which are higher or lower homologue perfluoroalkyl iodides can occur using as reactants any perfluoroalkyl iodides initially present in the process as reactants, or formed as intermediates in the process.

The reactant compounds of formula (II) are commercially available from E. I. du Pont de Nemours and Company, Wilmington, Del. or can be produced according to a telomerization process as described in U.S. Pat. No. 3,234,294, herein incorporated by reference. Compounds of formula (III), pentafluoroethyl iodide, can be purchased from Sigma-Aldrich, St. Louis, Mo., or can be produced according to a synthesis process as described in U.S. Pat. No. 3,132,185, herein incorporated by reference.

The present invention is carried out by passing liquid or gas streams of compounds of formula (II) and liquid or gas streams of formula (III) through a heated reactor. The streams can be diluted with an inert gas, such as nitrogen. The reactor can be a stand-alone process, or can be coupled to the end of a telomerization process to produce compounds of formula (I). The present invention can also be conducted as a batch process in addition to a continuous feed process. The reactants are typically pumped through tubing, such as stainless steel, preferably to a preheater. The reactants are employed such that the molar ratio of formula (III) to formula (II) is less than 1.0. The reactants are vaporized at about 200° C., and preheated in stages from about 200° C. up to the desired reaction temperature. The reactants are thoroughly mixed using conventional equipment, such as a static mixer, and may be sampled for online analysis. Additional heating can be employed during mixing. The mixture is then conducted through a reactor wherein it is heated to a temperature of from about 450° C. to about 500° C. The residence time in the reactor is from about 0.1 to about 10 seconds. The product stream exiting the reactor is then cooled to <250° C., and may be sampled for online analysis. The cooled product stream is then transferred to containers for storage or distribution. The product stream, including any byproducts and unreacted materials can be recycled back into the process without isolation to improve efficiency.

The ratio of the reactant compounds of formula (III) to formula (II) is less than 1.0; preferably it is less than 0.7. In an embodiment, the ratio of formula (III) to formula (II) is less than 0.6, or less than 0.5. In an embodiment, the ratio of formula (III) to formula (II) is zero, meaning the process is carried out in the absence of formula (III), C2-I. The residence time of the reactants in the reactor may range from as low as 1.5 seconds, or 1.0 seconds, or 0.6 seconds, or 0.5 seconds, or even as low as 0.4 seconds, or 0.1 seconds; and may range from as high as 30 seconds or as high as 10 seconds, or 9 seconds, or 7 seconds, or 6.5 seconds, or 5 seconds. The residence time of the reactants in the reactor is preferably from about 0.1 to about 10 seconds, more preferably from about 0.4 to about 9 seconds, and more preferably from about 0.6 to about 7 seconds. The reaction is conducted at temperatures that range from as low as 400° C., or as low as 450° C., or 460° C., or 470° C., or 480° C., or from 485° C.; and may range up to as high as 460° C., or as high as 470° C., or 480° C., or 485° C., or 490° C., or as high as 495° C., or 500° C. The reaction preferably is conducted at temperatures of from about 470° C. to about 495° C., more preferably from about 480° C. to about 495° C.; and even more preferably from about 485° C. to about 495° C. In an embodiment, the preferred reaction temperature is 490° C. When using a temperature that is lower within the above cited range, a longer residence time can be employed, such as, up to 30 seconds. At higher temperatures within or above the above cited range a residence time of less than one second can be employed.

The present invention is useful in increasing the selectivity for formula (I) and the process can be employed with or without use of added iodine ($I_2$) as a reactant. An increase in selectivity is accomplished while also minimizing the formation of perfluoroalkanes (byproduct). Iodine use tends to decrease the overall conversion of reactants to desired products and also could cause the formation of 1-hydroperfluoroalkanes, which is avoided in the process of the present invention. Iodine also can cause line plugging due to iodine condensation, and introduces the need for recycling or neutralizing the unreacted iodine. In the process of the present invention the selectivity for formation of formula (I) is a minimum of 40 mol % without the addition of iodine as a reactant, preferably the minimum is 45 mol %, more preferably the minimum is 50 mol %, or even 52 mol % or 55 mol %. The amount of perfluoroalkane obtained using the process of the present invention is a maximum of about 25 mol %, preferably a maximum of about 20 mol %, and more preferably a maximum of about 15 mol % or 10 mol %.

The increased selectivity for formula (I) in the process of the present invention is useful in generating commercial quantities of the shorter chain perfluoroalkyl iodides economically for use as starting materials in the preparation of surface modifying products. Increased selectivity results in a larger amount of desirable perfluoroalkyl iodides of formula (I) compared to the higher homologue perfluoroalkyl iodides, wherein the higher homologue perfluoroalkyl iodides have 10 or more carbons, and perfluoroalkanes. This further decreases production time by decreasing the number of passes needed to convert longer chain perfluoroalkyl iodides into compounds of formula (I). 1-Hydroperfluoroalkanes were not detected in the present invention. Perfluoroalkanes and 1-hydroperfluoroalkanes are inert and cannot be used as starting materials to produce surface modifying products.

The process of the present invention provides perfluoroalkyl iodides of formula (I) containing four and six carbons in the perfluoroalkyl chain. This is beneficial for use in producing surface modifying products containing the corresponding short perfluoroalkyl chains.

MATERIALS AND TEST METHODS

Perfluoro-octyl iodide (C8-I), and mixtures of C8-I with C10-I can be produced according to a telomerization process as described in U.S. Pat. No. 3,234,294, herein incorporated by reference. Pentafluoroethyl iodide (C2-I) can be produced according to a synthesis process as described in U.S. Pat. No. 3,132,185, herein incorporated by reference. Iodine is commercially available from Woodward Iodine Corporation, Woodward, Okla., or from Tamaya Chemical Corporation (Virginia Beach, Va.).

Analysis of the products was carried out by gas chromatography equipped with a flame ionization detector (GC-FID) and results are given in mol %, unless otherwise noted.

EXAMPLES

Examples 1-9

Perfluoro-octyl iodide (or a mixture containing predominantly C8-I and C10-I, composition given below in Table 2) and pentafluoroethyl iodide (if any) were pumped through stainless steel tubing (¼") and combined into one stream, which was mixed and vaporized at a temperature of about 200° C. The vaporized feed mixture was then passed through a series of preheaters to raise the temperature in stages from 200° C. to the specified reaction temperature. The heated mixture then flowed into a reactor (INCONEL 600, ¼" to ½") set at 490° C. The reactor length, diameter and/or the flow rate of the reactants were varied to allow for the desired residence time. Periodic online samples were taken from both the feed mixture and the product mixture, and analyzed by GC-FID. Upon exiting the reactor, the product stream was cooled to about 200° C. and transferred into a storage tank. Selectivity for C4-I and C6-I was based on total moles of $F(CF_2CF_2)_2$—I and $F(CF_2CF_2)_3$—I produced as a percentage of the total moles of all converted perfluoroalkyliodide reactants, and is expressed as a percentage (Table 1). The combined mol % of all perfluoroalkanes was also recorded.

For each Example, the molar ratios of pentafluoroethyl iodide to perfluoro-octyl iodide (or to the mixture containing predominantly C8-I and C10-I), reaction temperatures (° C.), residence times (seconds), and selectivity data are listed in Table 1.

Examples 10-12

Examples 10-12 were conducted using the process of Examples 1-9 except that iodine was used as an additional reactant. The ratios of pentafluoroethyl iodide to perfluoro-octyl iodide (or to the mixture containing predominantly C8-I and C10-1), reaction temperatures (° C.), amounts of iodine, and residence times (seconds) are listed in Table 1. In Table 1, the amount of iodine is shown as a mole ratio (the ratio of reactant moles of iodine to reactant moles of combined perfluoroalkyl iodide reactants). The iodine was pumped through stainless steel tubing (¼") and vaporized at a temperature of about 200° C. The iodine stream was then mixed with the pre-mixed and vaporized perfluoroalkyl iodide stream. The mixed iodine-perfluoroalkyliodide vapor stream was then flowed through the staged preheaters and the reactor as described in Example 1, and was processed as described in Example 1. Selectivity data are listed in Table 1.

Examples 13-16

Examples 13-16 followed the same procedure as above for Examples 1-9, except the reactor temperature was set at 470° C.

Comparative Examples, Comp. 1-Comp. 22

Comparative Examples, Comp. 1-Comp. 22, were conducted using the process of Examples 1-9 except that a higher ratio of formula (III) to formula (II) was employed for the Comparative Examples. The ratios of pentafluoroethyl iodide to perfluoro-octyl iodide (or to the mixture containing predominantly C8-I and C10-1), reaction temperatures (° C.), residence times (seconds) and selectivity data are listed in Table 1. For the Comparative Examples, lower selectivity for C4-I and C6-I was obtained along with a higher level of undesirable byproducts (particularly perfluoroalkanes).

TABLE 1

Selectivity for Formula (I) at Varying C2-I/C8-I Ratios[1,2]

| Run | Temp. (° C.) | Reaction Time (sec) | Iodine Co-feed (ratio of $I_2$ to total perfluoroalkyl iodide) | Molar Ratio of C2-I to C8-I (or to C8-$I_{\&+}$)* | Selectivity C4-I and C6-I (mol %) | Selectivity Perfluoroalkanes (mol %) |
|---|---|---|---|---|---|---|
| Ex. 1* | 490 | 1.7 | | 0 | 57.2 | 3.8 |
| Ex. 2 | 490 | 1.6 | | 0 | 57.1 | 9.2 |
| Ex. 3* | 490 | 0.6 | | 0 | 56.7 | 5.7 |
| Ex. 4* | 490 | 1.8 | | 0 | 55.5 | 5.7 |
| Ex. 5* | 490 | 6.4 | | 0 | 55.3 | 5.6 |
| Ex. 6 | 490 | 0.5 | | 0 | 50.8 | 11.9 |
| Ex. 7 | 490 | 5.1 | | 0.45 | 50.1 | 16.6 |
| Ex. 8* | 490 | 0.6 | | 0.48 | 48.6 | 12.8 |
| Ex. 9* | 490 | 0.6 | | 0.58 | 47.3 | 14.2 |
| Comp. 1 | 490 | 4.0 | | 1.07 | 45.8 | 21.9 |
| (Comp. 2) | 490 | 4.2 | | 1.11 | 51.4 | 24.2 |
| Comp. 3* | 490 | 3.5 | | 1.30 | 51.7 | 17.9 |
| Comp. 4 | 490 | 4.8 | | 1.59 | 40.1 | 23.7 |
| Comp. 5 | 490 | 4.8 | | 1.75 | 40.5 | 22.8 |
| Comp. 6 | 490 | 4.1 | | 2.07 | 45.5 | 22.4 |
| (Comp. 7) | 490 | 4.2 | | 2.22 | 46.6 | 26.6 |
| Comp. 8* | 490 | 4.0 | | 2.23 | 45.4 | 21.8 |
| Comp. 9 | 490 | 3.9 | | 2.80 | 38.7 | 25.0 |
| Comp. 10 | 490 | 2.6 | | 3.84 | 40.4 | 25.6 |
| Comp. 11* | 490 | 3.2 | | 3.95 | 43.2 | 24.0 |
| Comp. 12 | 490 | 3.4 | | 3.96 | 42.0 | 25.4 |
| Comp. 13 | 490 | 3.7 | | 4.21 | 41.9 | 25.4 |
| Comp. 14 | 490 | 4.0 | | 4.43 | 34.8 | 24.9 |
| (Comp. 15) | 490 | 4.1 | | 4.44 | 49.2 | 25.2 |
| Comp. 16 | 490 | 5.0 | | 5.45 | 36.5 | 28.3 |
| Comp. 17* | 490 | 2.7 | | 8.97 | 34.1 | 30.0 |
| Comp. 18 | 490 | 3.9 | | 9.45 | 34.5 | 29.9 |
| Comp. 19 | 490 | 4.4 | | 10.23 | 25.7 | 33.0 |
| Comp. 20 | 490 | 4.5 | | 10.89 | 21.8 | 36.8 |
| Comp. 21 | 490 | 5.1 | | 11.61 | 25.8 | 34.8 |
| (Comp. 22) | 490 | 4.2 | | 17.20 | 21.5 | 39.1 |
| Ex. 10* | 490 | 1.0 | 0.27 | 0 | 72.3 | 4.3 |
| Ex. 11 | 490 | 4.3 | 0.15 | 0.44 | 55.8 | 8.4 |
| Ex. 12 | 490 | 4.9 | 0.12 | 0.44 | 57.1 | 11.9 |
| Ex. 13* | 470 | 0.6 | | 0 | 69.7 | 3.8 |
| Ex. 14 | 470 | 5.3 | | 0 | 63.0 | 10.9 |
| Ex. 15* | 470 | 1.7 | | 0 | 56.1 | 6.5 |
| Ex. 16 | 470 | 5.2 | | 0.45 | 54.1 | 16.0 |

[1]The processes were run using a pure C8-I as the starting perfluoroalkyl iodide (formula II), except where the Run Number (Example No.) is marked with an asterisk (*) in column 1. For these examples the process was run using a synthetic mixture of C8-I and C10-I (the composition is given below in Table 2).
[2]The Run Numbers (Example No.s) shown in parentheses represent prior art data (U.S. Pat. No. 8,258,354 B1).

TABLE 2

Typical Composition of Mixed C8-I/C10-I Reactant
(Examples 1, 3, 4, 5, 8, 9, 10, 13, 15, & Comparative
Examples 3, 8, 11, 17)

| Component | Mole % |
|---|---|
| C6-I | 1.0 |
| C8-I | 78.6 |
| C10-I | 15.4 |
| C12-I | 2.6 |
| C14-I | 0.5 |
| C16-I | 0.1 |
| Perfluoroalkanes | 1.8 |
| Total | 100.0 |

Many variables affect the process, and, accordingly, the selectivity of the C4-I and C6-I products. Previous studies have shown that the addition of iodine causes an increase in selectivity but also decreases overall conversion of reactants to the desired products. For example, the data presented graphically in FIG. 1 demonstrate that the absence of iodine results in a combined C4-I and C6-I selectivity that is some 15-20% lower than that produced when iodine is present at levels of normal usage (>0.1 mol iodine/mol perfluoroalkyl iodide reactants).

However, as noted earlier, the use of added iodine in such processes is problematic from the practical standpoint due to side reactions producing undesirable inert by-products (among other issues). Accordingly, some manufacturers would prefer a process that does not include iodine. FIG. 1 shows the data for which the ratio of C2-I to C8-I is 2.1 (mols of C2-I to mols of C8-I). Those skilled in the art have assumed that a lower perfluoroalkyl iodide "TFE trap" species (e.g. C2-I) was required in such processes in order to capture TFE fragments as they were cleaved from the higher perfluoroalkyl iodide reactant (e.g. C8-I and higher homologue species) thereby avoiding production of even higher perfluoroalkyl iodides and undesirable perfluoroalkane coupling products. The assumption in the art has been that removal of the TFE trap species altogether would also dramatically reduce the combined C4-I and C6-I selectivity (in analogous fashion to that observed for the effect of iodine—see FIG. 1: reduced selectivity for C4-I and C6-I at zero iodine). Thus, both DE 4,410,551 A1 and U.S. Pat. No. 8,258,354 B2 disclose improved processes to produce the C4-I and C6-I products using reactants that are required to be a mixture of both higher and lower perfluoroalkyl iodides. That is, they specifically require a "TFE trap" species.

Furthermore, teachings in the open literature have reported that, in the absence of C2 or other TFE trap species, the pyrolysis of perfluoro-alkyliodides results in approximately even distribution of higher and lower homologues in C2 increments either side of the starting chain length, as shown above in Reaction Scheme 2 (see, for example, A. Probst and K. Von Werner in: *Journal of Fluorine Chemistry*, 47, (1990), 163-173)

Applicants have surprisingly found that not only is the lower perfluoroalkyl iodide TFE trap species not required, but also that, at zero levels of the TFE trap species, the combined C4-I and C6-I selectivity can actually be increased compared to that obtained with the TFE trap species.

Figure 2:
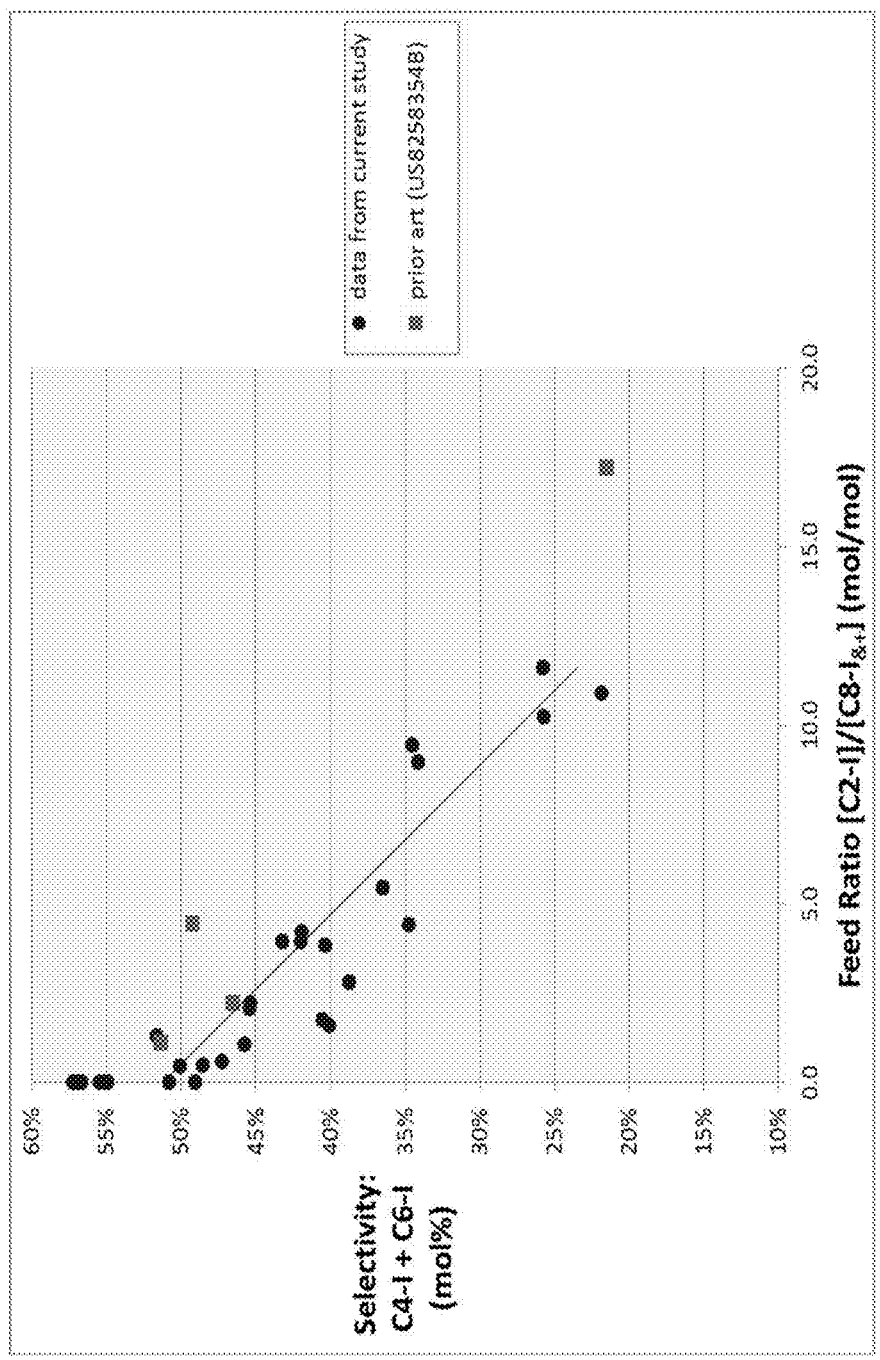
FIG. 2 shows a plot of selectivity for C4-I and C6-I produced in the process (y axis, in mol %) as a function of the amount of formula (III) TFE trap species present in the reactant (x axis, molar ratio of C2-I (formula (III), p=1), to higher perfluoroalkyl iodide, C8-I$_{\&+}$ (formula (II), m≥4)).

FIG. 2 shows this data graphically for the combined C4-I and C6-I selectivity resulting from varying ratios of C2-I to C8-I. Surprisingly, the C4-I and C6-I selectivity does not drop precipitously at a C2-I/C8-I ratio of zero (i.e. zero TFE trap) as is the case for zero iodine in FIG. 1. Instead the selectivity lies surprisingly higher.

Figure 3:
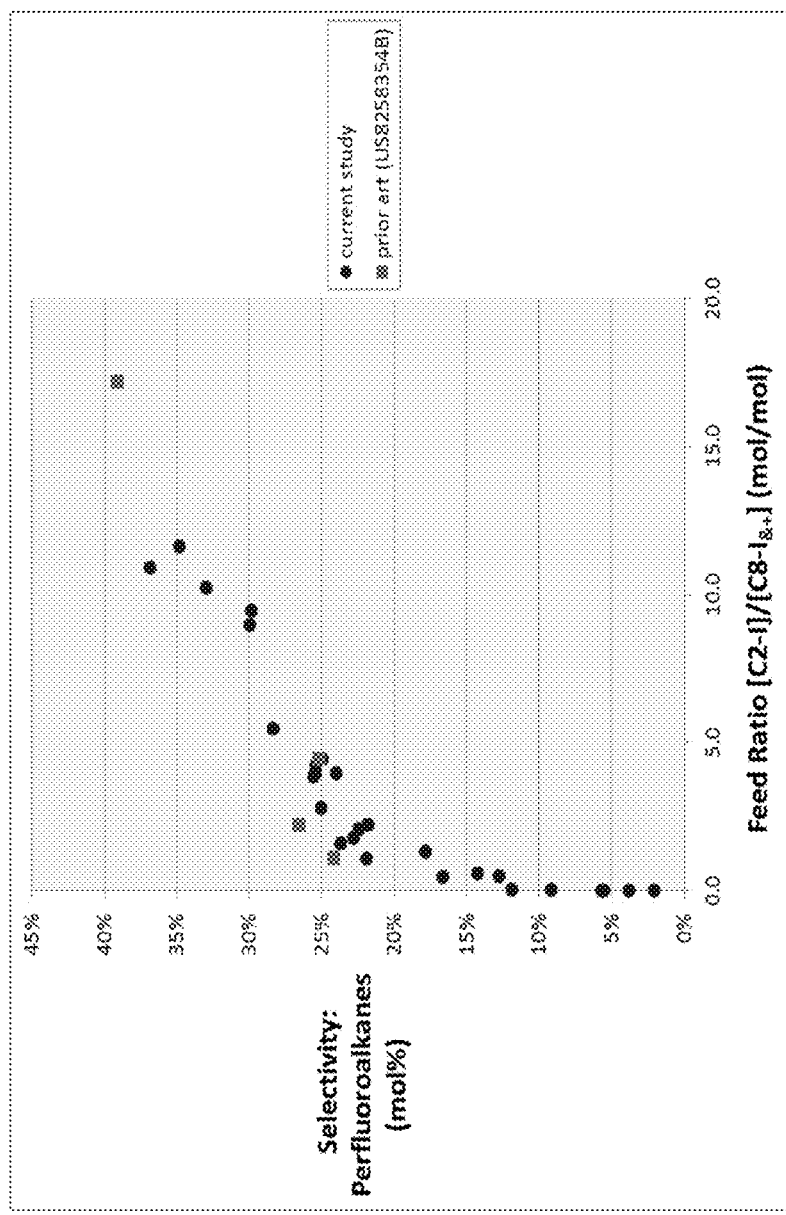
FIG. 3 shows a plot of selectivity for perfluoroalkanes produced in the process (y axis, in mol %) as a function of the amount of formula (III) TFE trap species present in the reactant (x axis, molar ratio of TFE trap species, C2-I (formula (III), p=1), to higher perfluoroalkyl iodide, C8-I$_{\&+}$ (formula (II), m≥4)).

Moreover, not only is the selectivity for C4-I and C6-I surprisingly high, but there is a very surprising additional benefit observed at low C2-I/C8-I ratios. FIG. 3 shows that the selectivity for the undesirable perfluoroalkane species drops off dramatically at C2-I/C8-I ratios of less than 1.0. This is important from a practical standpoint because an iterative process would either continue to accumulate the inert perfluoroalkanes (to the detriment of the final C4-I and C6-I yield), or the perfluoroalkanes would have to be removed as unrecoverable waste in large quantities.

The data show that the present invention produces high selectivity of $F(CF_2CF_2)_n-I$ where n is 2 or 3. Moreover, the process is operable for processes both with and without the use of added iodine. The inventive process negates the requirement to use a valuable lower perfluoroalkyl iodide compound as a TFE trap species and instead allows the direct thermolyzing of C8-I, or mixtures of C8-I and higher telomers, in order to prepare the desired C4-I and C6-I compounds. And finally, production of waste is greatly reduced, because the process produces very little of the inert perfluoroalkanes, which represent the largest yield loss in the process.

What is claimed is:

1. An improved process for producing perfluoroalkyl iodides of formula (I)

$$F(CF_2CF_2)_n-I \qquad (I)$$

wherein n is an integer from 2 to 3, wherein the improvement comprises thermolyzing at least one perfluoroalkyl iodide of formula (II), optionally in the presence of perfluoroethyl iodide, formula (III)

$$F(CF_2CF_2)_m-I \qquad (II)$$

$$F(CF_2CF_2)_p-I \qquad (III)$$

wherein m is an integer greater than or equal to 4, and p is 1, wherein a) the molar ratio of formula (III) to formula (II) is 0, b) the residence time is from 0.1 to 10 seconds, and c) the temperature is from 450° C. to 500° C.

2. The process of claim 1 wherein the selectivity for species (I) is greater than 45 mol %.

3. The process of claim 1 wherein the temperature is from 470° C. to 495° C.

4. The process of claim 1 wherein the residence time is held at from 0.4 to 9 seconds.

5. The process of claim 1 wherein the selectivity for species (I) is greater than 45 mol % without use of iodine as a reactant.

6. The process of claim 1 wherein the selectivity for perfluoroalkanes is less than 20 mol %.

7. The process of claim 6 wherein the selectivity for perfluoroalkanes is less than 10 mol %.

8. The process of claim 1, performed in the absence of a TFE trap species.

9. An improved process for producing perfluoroalkyl iodides of formula (I)

$$F(CF_2CF_2)_n-I \qquad (I)$$

wherein n is an integer from 2 to 3, wherein the improvement comprises thermolyzing, in the absence of a TFE trap species, at least one perfluoroalkyl iodide of formula (II), optionally in the presence of perfluoroethyl iodide, formula (III)

$$F(CF_2CF_2)_m-I \qquad (II)$$

$$F(CF_2CF_2)_p-I \qquad (III)$$

wherein m is an integer greater than or equal to 4, and p is 1, wherein a) the molar ratio of formula (III) to formula (II) is 0, b) the residence time is from 0.1 to 10 seconds, and c) the temperature is from 450° C. to 500° C.

10. The process of claim 9 wherein the selectivity for species (I) is greater than 45 mol %.

11. The process of claim 9 wherein the residence time is held at from 0.4 to 9 seconds.

12. The process of claim 9 wherein the temperature is from 470° C. to 495° C.

\* \* \* \* \*